US006662818B2

(12) United States Patent
Paul et al.

(10) Patent No.: US 6,662,818 B2
(45) Date of Patent: Dec. 16, 2003

(54) PROGRAMMABLE TRACKING PRESSURE REGULATOR FOR CONTROL OF HIGHER PRESSURES IN MICROFLUIDIC CIRCUITS

(75) Inventors: Carlton H. Paul, Groton, MA (US); Guy B. Praria, Wayland, MA (US); Jeffrey H. Stokes, Franklin, MA (US)

(73) Assignee: PerSeptive Biosystems, Inc., Framingham, MA (US)

( * ) Notice: Subject to any disclaimer, the term of this patent is extended or adjusted under 35 U.S.C. 154(b) by 81 days.

(21) Appl. No.: 10/061,985

(22) Filed: Feb. 1, 2002

(65) Prior Publication Data

US 2003/0145886 A1 Aug. 7, 2003

(51) Int. Cl.⁷ .......................... G05D 11/13; G01L 13/02
(52) U.S. Cl. .................. 137/14; 137/101.19; 137/806; 137/557; 137/98; 73/736
(58) Field of Search .................. 137/98, 100, 101.19, 137/594, 557, 12, 14, 806, 833; 73/736; 417/46, 53; 210/198.2; 422/70, 100, 103

(56) References Cited

U.S. PATENT DOCUMENTS

| 4,218,925 A | | 8/1980 | DiMonizio, Jr. | |
| 4,330,003 A | * | 5/1982 | D'Alonzo | 137/100 |
| 4,593,703 A | * | 6/1986 | Cosman | 600/561 |
| 4,798,089 A | * | 1/1989 | Frick et al. | 73/706 |
| 5,320,139 A | * | 6/1994 | Paul et al. | 137/597 |
| 5,471,884 A | * | 12/1995 | Czarnocki et al. | 73/720 |
| 5,888,050 A | * | 3/1999 | Fitzgerald et al. | 417/46 |
| 5,939,640 A | | 8/1999 | Hauser | |
| 5,980,755 A | * | 11/1999 | Roberts et al. | 210/741 |
| 6,070,607 A | | 6/2000 | Casey | |
| 6,193,471 B1 | * | 2/2001 | Paul | 417/53 |
| 6,401,541 B1 | * | 6/2002 | Kurtz | 73/716 |
| 6,453,928 B1 | * | 9/2002 | Kaplan et al. | 137/14 |
| 6,487,912 B1 | * | 12/2002 | Behm et al. | 73/753 |

FOREIGN PATENT DOCUMENTS

| DE | 101 01 180 | 9/2002 |
| EP | 0 317 809 | 4/1988 |
| WO | WO 91/07712 | 5/1991 |
| WO | WO 01/63270 | 8/2001 |

* cited by examiner

Primary Examiner—Michael Mar
Assistant Examiner—Ramesh Krishnamurthy
(74) Attorney, Agent, or Firm—Andrew T. Karnakis

(57) ABSTRACT

Regulator for precision control of pressure based on a means of measuring pressure differentials. More specifically, the present invention provides a pressure control that tracks a relatively high background pressure, and applies a positive or negative offset to create the small pressure differentials that can be utilized to transport fluids within a capillary network. The present invention is also directed to a method of controlling microfluidic elements (such as donut cavities) with a high degree of precision. In high performance liquid chromatography applications, this is accomplished using tracking pressure regulators to measure and respond to the difference between the liquid pump pressure and the regulated pneumatic pressure.

11 Claims, 5 Drawing Sheets

PROGRAMMABLE TRACKING PRESSURE REGULATOR FOR CONTROL OF HIGHER PRESSURES IN MICROFLUIDIC CIRCUITS

BACKGROUND OF THE INVENTION (a) Field of the Invention

This invention relates to a programmable tracking pressure regulator and method particularly useful for pressure control in apparatus utilizing the formation, control and movement of small volumes of liquid. More particularly, this invention relates to a programmable tracking pressure regulator and method capable of high-precision pressure control in microfluidic networks, even at high operating pressures, for uses such as capillary chromatography.

(b) Description of Prior Art

Fluid transport in microfluidic circuits is normally effected in one of two ways: either by applying pressure differences between selected points in the circuit, or by applying voltage differences between selected points. The application of pressure results in the classical Hagen-Poiseuille laminar flow distribution in capillaries, whereas the application of voltage results in electrokinetic pumping and plug flow. In both cases, however, the control of fluid transport at the scale of capillaries has been handicapped by the absence of microscopic fluid gates. In branched fluid circuits, in the absence of a means to stop the flow in certain directions, there is no way to isolate different parts of the fluid circuit.

It has been proposed to provide mechanical gates in capillary circuits, wherein the valve closures consist of diaphragms or similar sealing members. However, at capillary scales the mechanical valves are unreliable and difficult to fabricate, particularly if alignment is required between parts. Mechanical valves have not been useful at the scale of nanoliter volumes.

It has also been proposed to use non-mechanical means to control fluid movements in capillaries. For example, the concept of utilizing menisci to control fluid movements in capillaries has been utilized in devices such as in the Lang-Levy micropipette.

U.S. Pat. No. 6,193,471, the disclosure of which is hereby incorporated by reference, discloses a controllable method for creating menisci in a liquid capillary, for removing menisci from a liquid capillary, and for external control of the hydrostatic pressure within a capillary segment. More specifically, the '471 patent discloses a process and system for transporting small volumes of liquid samples such as at the nanoliter level. The process and system permits the inclusion and/or the removal of menisci from a liquid sample and also permits the transport of exact small volumes of liquid sample from a storage means to a point of use in order to permit precise treatment of the sample such as for analysis or reaction.

Pressure balancing can be used to control fluid transport in capillary networks as described in the '471 patent. A shallow, disk-shaped cavity or "donut" positioned along the track of a capillary will cause a liquid stream to split and flow around the periphery of the cavity. A separate channel perpendicular to the disk along the axis of the disk allows pressure access to the liquid. An external pressure source can be impressed on the meniscus of the split-stream of the liquid, thereby controlling the hydrostatic pressure of the liquid in the capillary. When control cavities or "donuts" are placed at opposite ends of a capillary, they can be employed to produce a pressure gradient along that capillary that directs movement of liquid through the capillary. More specifically, a storage volume having a height of a capillary is in fluid communication with at least two capillary conduits. The storage volume has a width larger than the width of a capillary so that the storage volume is capable of retaining a larger volume of liquid as compared to the volume stored in a capillary. The storage volume also is in fluid communication with a gas having a controlled pressure thereby permitting the storage volume to function as a pressure control point on a liquid in the storage volume. A meniscus is formed within the storage volume at the interface of a liquid directed to the storage volume from an inlet capillary conduit and the gas supplied to the storage volume. The liquid is passed from the storage volume into an outlet capillary conduit. The liquid in the outlet capillary conduit extends from the storage volume to a capillary gate at the end of the outlet capillary conduit, where a second meniscus is formed on the liquid surface in the outlet capillary conduit. The capillary gate functions as a valve. Control of liquid flow is based on the fact that the meniscus forces at the capillary gate arrest the flow of liquid in the outlet capillary conduit unless hydrostatic pressure exerted on the liquid in the outlet capillary conduit exceeds the meniscus forces.

For certain applications, such as providing the pressure differentials between microfluidic donuts, the control pressure differentials must be fairly small. At feature dimensions on the order of micrometers, the meniscus pressure in a capillary is about 1 psi. In order to use donuts and capillary forces at higher pressures, especially at the much higher pressures typical of high performance liquid chromatography, there must be some means for programmable, high-precision pressure control (e.g., ±0.01 to ±0.1 psi resolution on a common mode pressure of 2000 psi). The response time must be fast (e.g., within tenths of a second), but programmable control implies that the regulator must be able to rapidly increase or decrease the pressure as the circumstances dictate. In some cases, the regulator must be able to pull the pressure below atmospheric pressure.

It therefore would be desirable to provide a programmable, high-precision pressure regulator suitable for controlling small pressure differentials in microfluidic circuits notwithstanding the presence of relatively high common mode pressures.

SUMMARY OF THE INVENTION

The problems of the prior art have been overcome by the present invention, which provides a regulator for high precision control of pressure based on a means of measuring pressure differentials. More specifically, the present invention provides a pressure control that tracks a relatively high background pressure and applies a positive or negative offset to create the small pressure differentials that can be utilized to transport fluids within a capillary network. The present invention is also directed to a method of controlling pressure differences between connected pressure control nodes (such as donut cavities) with a high degree of precision. This is accomplished using tracking pressure regulators to measure and respond to the difference between a liquid pump pressure and a regulated pneumatic pressure.

Features

The present invention provides a compact, rugged, low cost, regulator for high precision control of pressure.

The present invention also provides a means of measuring multiple pressure differentials.

The present invention also provides a means of measuring multiple pressure differentials under a high common mode pressure.

The present invention also provides a means of controlling multiple pressure differentials.

The present invention also provides a means of controlling multiple pressure differentials under a high common mode pressure.

The present invention also provides an individually programmable means of controlling multiple pressure differentials under a high common mode pressure.

The present invention also provides a temperature compensated means of controlling multiple pressure differentials under a high common mode pressure.

The present invention also provides a means of controlling multiple pressures that track a relatively high background pressure, and applying positive or negative offsets to create small pressure differentials.

The present invention also provides a method of sensing and measuring very small pressure differences between very small volumes.

The present invention also provides a means of easily and rapidly changing the composition of the control fluid without danger of contamination.

DESCRIPTION OF SPECIFIC EMBODIMENTS

In order to use capillary gates or "donuts" and capillary forces at higher pressures, especially at much higher pressures typical of high performance liquid chromatography (HPLC), there must be some means for programmable, high-precision pressure control (e.g., ±0.01 psi resolution against a background pressure as much as 2000 psi). In addition, the response time must be fast (e.g., within tenths of a second), yet the programmable control must be able to rapidly increase and decrease the pressure, and in some cases, pull the pressure below atmospheric pressure. Furthermore, for HPLC applications, the volume available for measuring the mobile phase pressure must be very small because the composition of the mobile phase is changing. The tracking pressure regulator in accordance with the present invention addresses these issues.

Figure 1A:
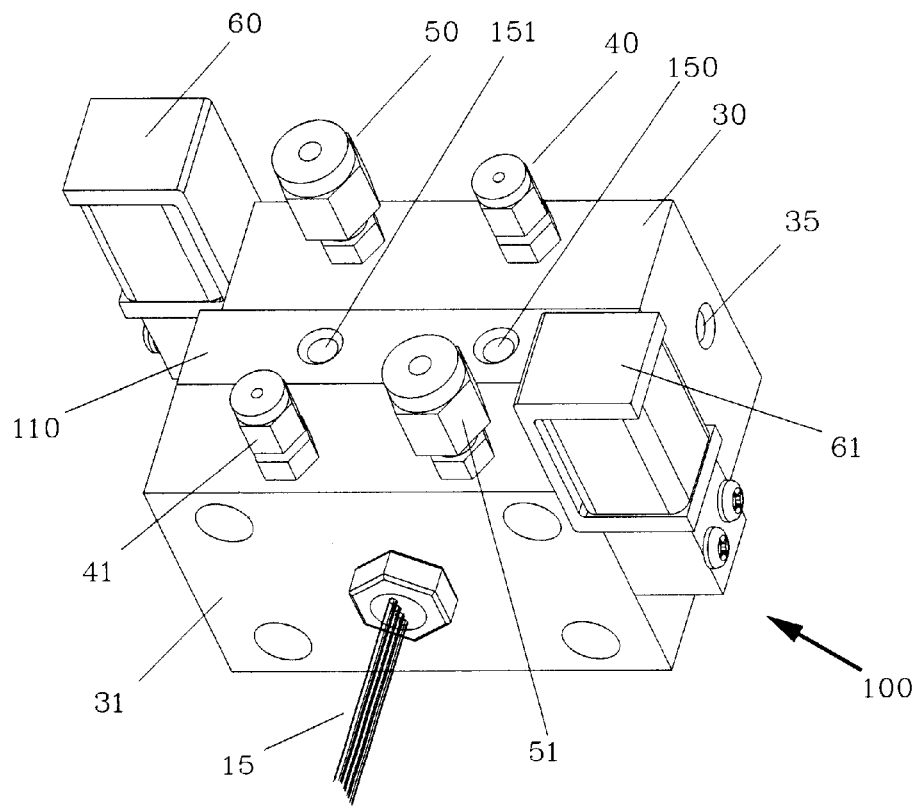
FIG. 1A is a perspective view of the tracking pressure regulator assembly used in the present invention.
Figure 1B:
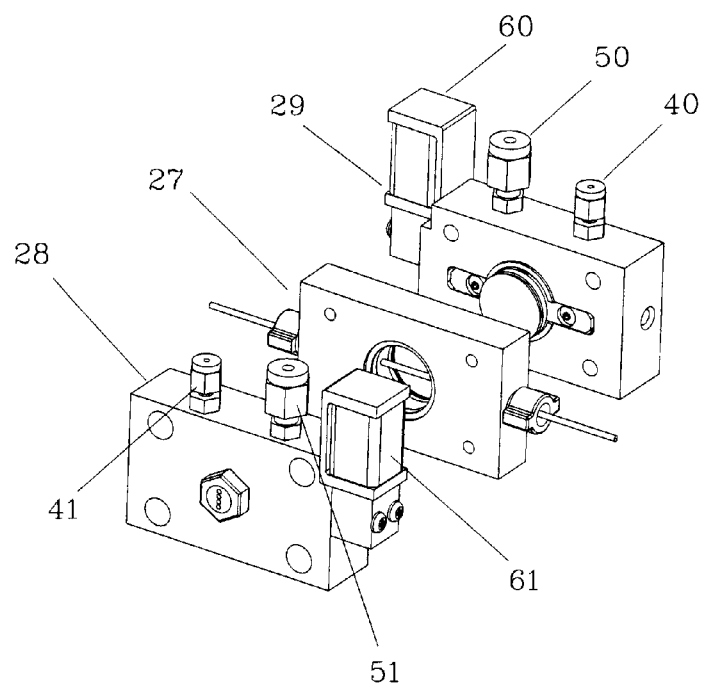
FIG. 1B is an exploded view of assembly 100, indicating the three modules constituting this assembly.

Turning now to FIG. 1A, there is shown a tracking pressure regulator assembly 100 in accordance with one embodiment of the present invention. The assembly is a high-pressure housing that meets the requirements of the present invention and has application in high performance liquid chromatography. In this embodiment, two pressure transducers are used in order to regulate the pressure at two different locations of a microfluidic network relative to a third location. Referring briefly to FIG. 1B, the assembly comprises two identical end modules 28, 29 attached to a middle module 27. Each end module 28, 29 includes a voltage sensitive orifice valve 60, 61 and fittings 40, 41, 50, 51, preferably Swaglock® fittings, detailed below. The middle module includes filling ports 150, 151 as shown and as discussed in greater detail below.

Figure 2:
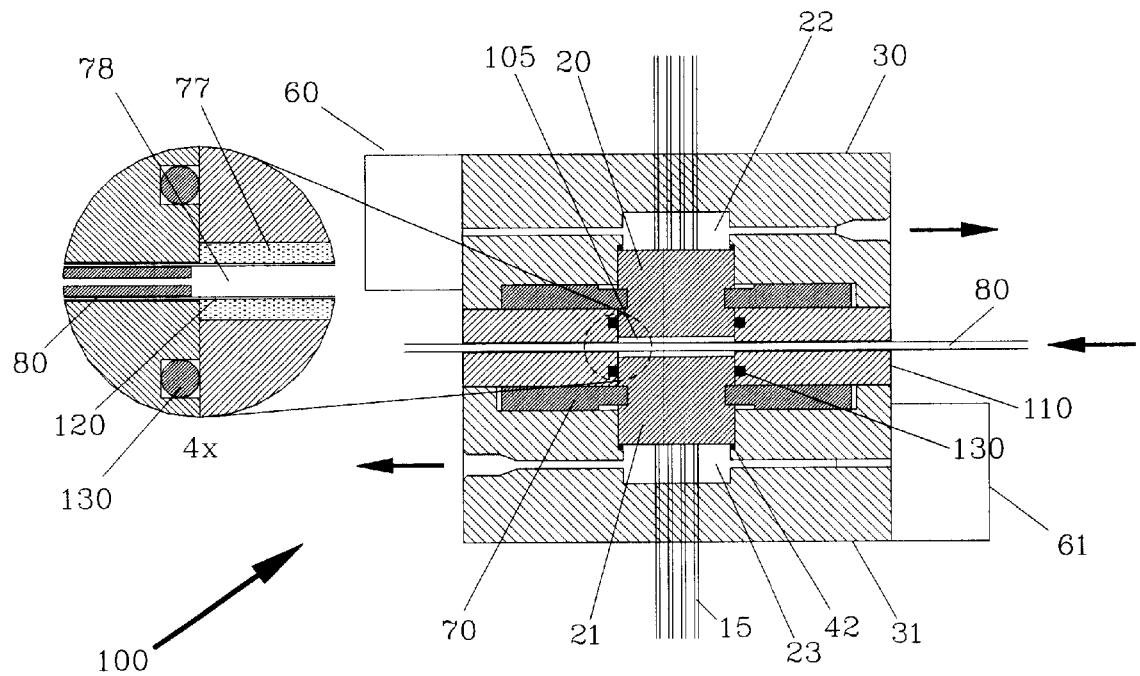
FIG. 2 is a horizontal cross-sectional view of the assembly shown in FIG. 1A.

With reference to FIG. 2, the entire assembly 100 of FIG. 1A is shown in a horizontal cross section. Two gauge-pressure transducers 20, 21 are mounted in assembly 100 in a back-to-back configuration. The transducers are separated by a shallow cavity 105 that is filled with a substantially incompressible fluid 77 such as silicon oil. A flattened, flexible thin-walled tube 120 carrying the mobile phase 78, a liquid under high pressure, passes through cavity 105. Pressure within tube 120 is transmitted, through the walls of tube 120 and thus through substantially incompressible fluid 77, to transducers 20, 21. The term "substantially incompressible" is used herein to mean any fluid that is sufficiently incompressible so as to transmit the pressure within the tube to the transducers without significant loss. Any volume reduction as a result of compression in the "substantially incompressible" fluid is replaced with additional volume of mobile phase flow in thin walled tube 120. Thin walled tube 120 is able to expand sufficiently without added stress to prevent restraining the pressure of the mobile phase fluid. Correspondingly, any variations in volume as a result of temperature changes are compensated for by opposite variations in volume of the mobile phase flow 78. Such variations, either as a result of compression or temperature changes, have no effect on the accuracy of the transducer.

Those skilled in the art will appreciate that tube 120 and incompressible fluid 77 are not needed if mixing of fluid and minimizing of the volume are not problematic in the particular application. Thus the fluid could be transported directly into cavity 105.

A digital/analog electronic circuit (discussed in greater detail below with reference to FIG. 7) allows programmable control of the voltage sensitive orifice valves 60 and 61, still referencing FIG. 2. Each pressure transducer 20, 21 measures the difference in the pressure of the gas supply in an accumulator cavity (22 or 23) relative to the pressure of the mobile phase flow. In particular, pressure transducer 20 measures the pressure difference between accumulator cavity 22 and cavity 105, and pressure transducer 21 measures the pressure difference between accumulator cavity 23 and cavity 105. Consequently, two separate pressure differentials are obtained and two independent gas pressures are regulated electronically.

The tracking regulator uses a voltage sensitive orifice valve to control gas pressure. Suitable valves have a small, variable orifice, the size of which depends on the electrical current passing through the coil of the solenoid in the valve. This allows flow modulation, and thereby provides stable, pulseless regulation of the pressure. Unlike most other electrically actuated valves, which are designed to be either completely open or completely closed, these valves are intended to be partly open in a manner proportional to the control current. As a result, voltage sensitive orifice valves are particularly useful for devices such as pressure regulators because they can modulate the flow instead of delivering pulses. Such valves are commercially available, as for example from the Pneutronics division of Parker-Hannefin Corp. under the designation VSO$^R$ and are known to those skilled in the art. Standard "open-closed" valves can be used by modulating the duty cycle of the valves, if the resulting pressure pulses and noise can be tolerated.

Figure 7:
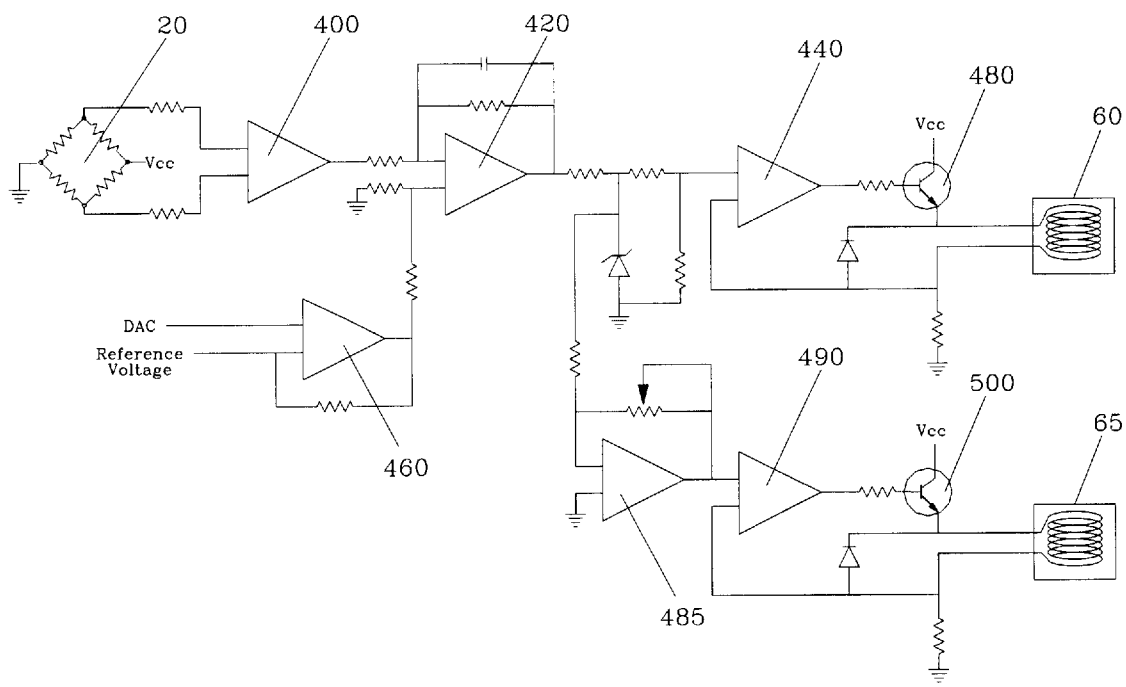
FIG. 7 is a schematic diagram of an electronic feedback circuit in accordance with the present invention.

The valves 60, 61 are preferably installed directly on the pressure housing as shown in FIG. 1A in order to eliminate a time lag that can cause pressure instability and oscillation of the feedback control. The gas supply enters the inlet of the valve and exits the orifice. The size of the orifice opening at any given time is determined by an electronic feedback loop as shown in FIG. 7 based upon the signal from the differential pressure transducer (20 or 21) associated with that particular valve (60 or 61).

Figure 3:
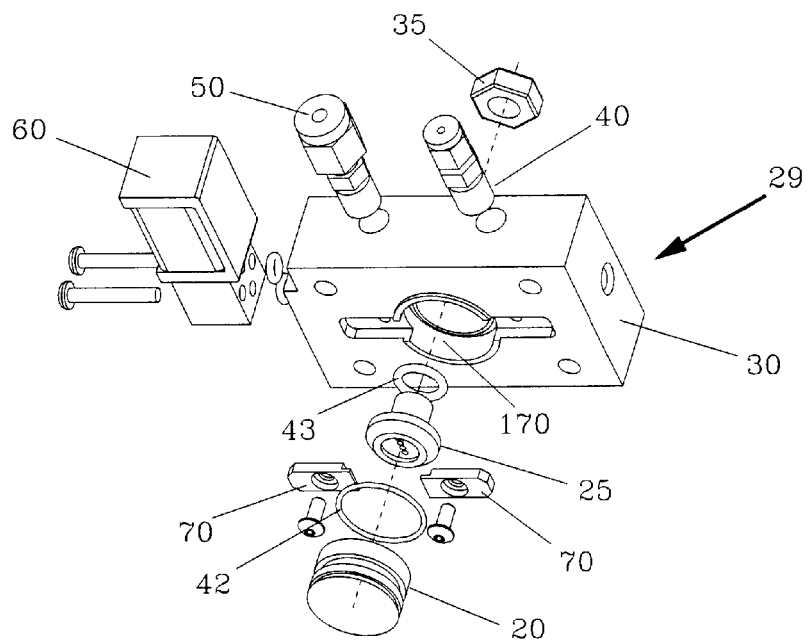
FIG. 3 is an exploded view of the end module 29 shown in FIG. 1B.

Turning now to FIG. 3, an exploded view of end module 29 of the tracking pressure regulator 100 is shown. End module housing 30 includes a central aperture 170 that aligns with the central aperture 160 of the middle module housing 110 (shown in FIG. 4) when the middle and end housings are attached. The pressure transducer 20 (with its diaphragm facing forward) is inserted into the aperture 170, pressing against an O-ring 42 and clamped in place with a pair of recessed tabs 70. A threaded feedthrough plug 25 is precisely positioned with respect to pressure transducer 20 and has slip-fit holes for the wires (not shown) from transducer 20. The feedthrough plug is sealed in place by means of an O-ring 43 and a nut 35 against end module housing 30. A Swaglock® fitting 40 connects small tubing to the housing 30 to provide vacuum for a controlled leak. The bore of the tubing that inserts into fitting 40 must be small (e.g., 0.015 inches ID) so as not to overload the high-pressure side. Another, larger Swaglock fitting 50 connects high-pressure tubing to the unit.

Figure 4:
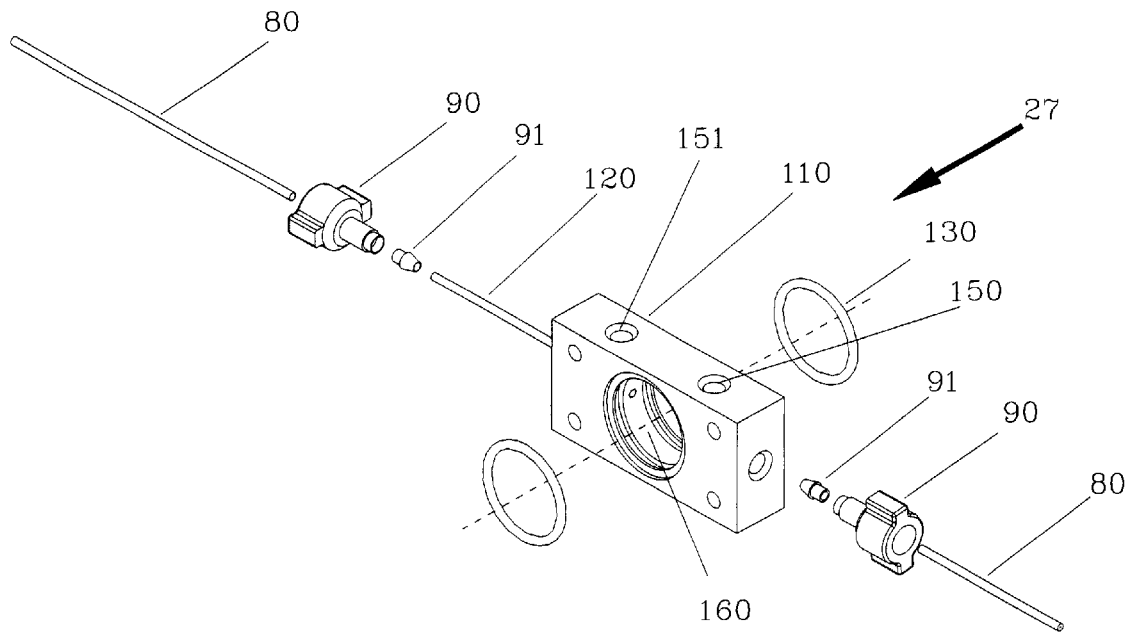
FIG. 4 is an exploded view of the middle module 27 shown in FIG. 1B.

FIG. 4 shows an exploded view of the middle module 27 of pressure regulator 100 in accordance with the present invention. Mobile phase 78(liquid) inlet tubing 80 is made of a material such as PEEK® capable of handing high pressures (e.g., pressures typical of mobile phases in HPLC). The tubing is coupled to the housing with high pressure fittings 90 and ferrules 91 modified to slip with respect to fittings 90 and having an enlarged bore to accommodate flexible, thin walled tubing 120. Tubing 120 has an inside diameter equal to the outside diameter (0.060 inches) of the inlet tubing 80, so that the tubing 120 can pull over inlet tubing 80 (best seen in FIG. 5). Tubing 120 is preferably thin-walled PTFE tubing (0.002 inches wall thickness). Housing 110 includes filling ports 150, 151 for the incompressible fluid. The central aperture 160 forms cavity 105 when transducers 20, 21 are inserted.

Figure 5:
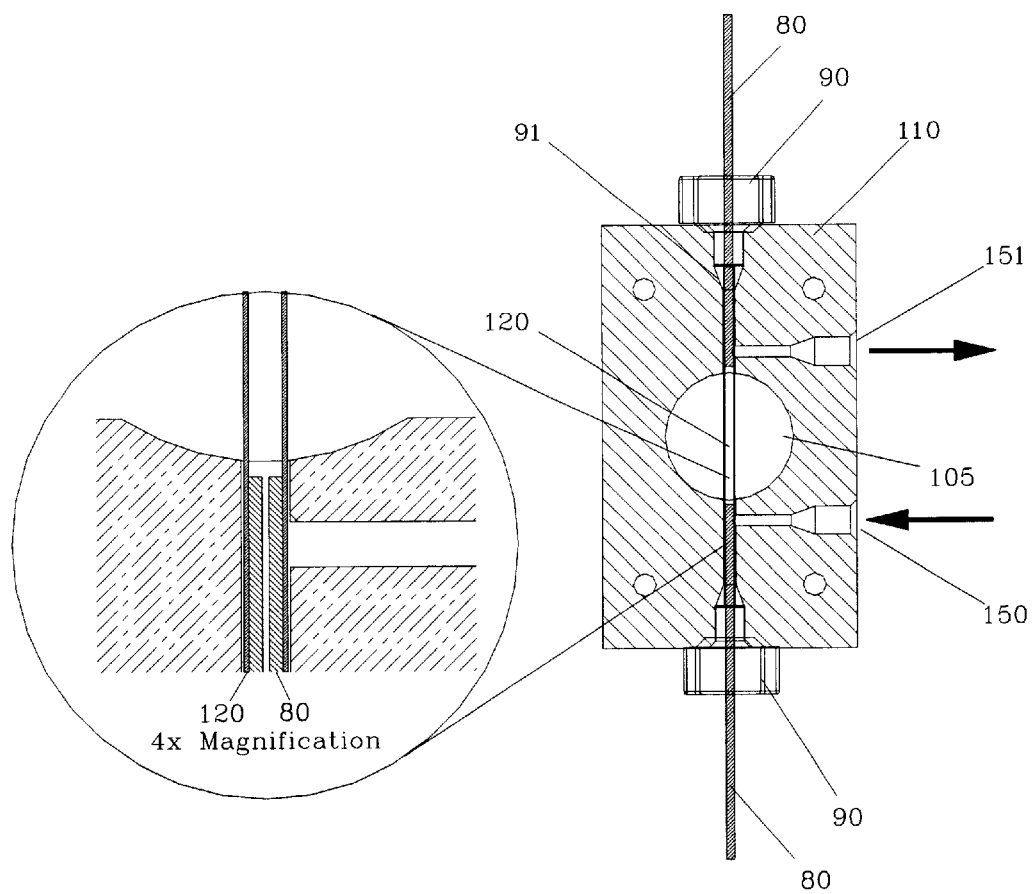
FIG. 5 is a cross-sectional view of the middle module 27 of the tracking pressure regulator shown in FIG. 4, showing how the assembly is filled with an incompressible fluid.

FIG. 5 is a cross-sectional view of the middle module 27 of FIG. 4. This view shows high-pressure mobile phase PEEK tubing 80 interrupted by a section of thin-walled PTFE tubing 120 within cavity 105. FIG. 5 shows how the incompressible fluid is introduced through inlet 150 into cavity 105 in such a way as to remove bubbles from the cavity, which would be detrimental to accurate measurement of the pressure within the mobile phase tubing. Introducing an incompressible fluid into entrance port 150 will force bubbles out of the channel, which is nearly a press-fit for tubing 80 and 120 (see magnified view in FIG. 5), leaving a film of incompressible fluid in this space. Trapped air will be pushed upward through cavity 105 and out of port 151, leaving the assembly devoid of bubbles. Ports 150, 151 are then sealed with high-pressure fittings.

Figure 6:
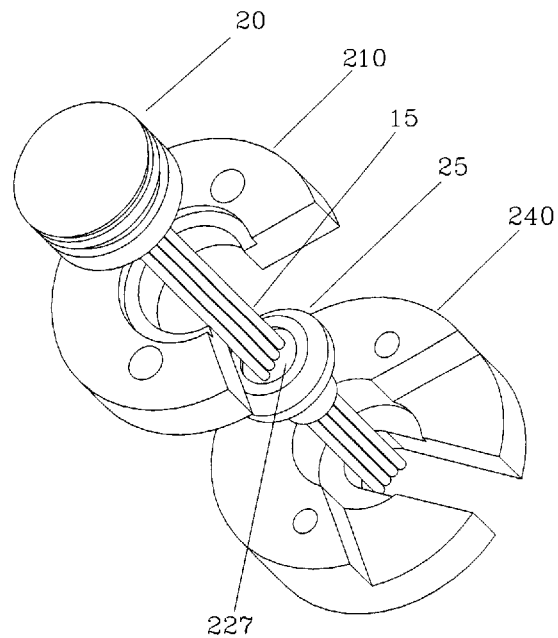
FIG. 6 is an exploded view of the pressure transducer of the tracking pressure regulator showing a mounting tool used to adjust the spacing between the pressure transducer and a feedthrough plug used to construct the pressure regulator of the present invention.

One problem encountered in constructing the apparatus of the present invention was getting the electrical leads from the pressure transducers 20, 21 out of assembly 100 without causing leaks, as both accumulator cavities 22, 23 are under high pressure. This was accomplished by designing a special tool, shown in FIG. 6, comprising a top part 210 and a bottom part 240 to adjust the spacing between pressure transducer 20 and feedthrough plug 25 while potting the wires in plug 25. The top part 210 of tool holds transducer 20 with its associated wire leads 15, and the bottom part 240 of the tool holds feedthrough plug 25. The tool is configured to simulate the spacing of these parts as they are assembled in end module 28, so that lead wires 15 can be potted in feedthrough plug 25 with the correct length and any necessary strain relief. Epoxy is injected into the dovetail depression 227 contained in feedthrough plug 25 to form a high-pressure seal around the wires.

FIG. 7 is a schematic diagram of a suitable electronic feedback circuit that can be used with the regulator of the present invention. The pressure transducer 20 is a temperature-compensated solid-state device configured as a Wheatstone bridge. The differential output from this transducer is amplified by an instrumentation amplifier 400 and compared by means of high-gain operational amplifier 420 to a reference signal supplied by operational amplifier 460. The DAC input to operational amplifier 460 represents the desired offset value (e.g. ±0.01 psi) that is to be maintained with respect to the high background pressure. The control signal from the operational amplifier 420 is converted by amplifier 440 and power transistor 480 into a current that drives the valve 60. If the gas pressure in the cavity 22 exceeds the mobile phase pressure by more than the programmed amount (i.e., as specified by the DAC reference), the current through the valve 60 will be reduced and the valve orifice will contract thereby reducing the pressure in cavity 22. Conversely, if the gas pressure in cavity 22 is below the programmed amount, the current will be increased and expand the orifice of the valve 60, causing the pressure to increase. The use of a DAC reference signal means that the pressure difference between the gas accumulator cavity (22 of FIG. 2) and the mobile phase is adjusted in small steps. The gas accumulator can have a higher pressure or a lower pressure than the mobile phase, and the difference can be changed in either direction very rapidly and reproducibly. While the foregoing description has been made with respect to transducer 20, the same principles of operation apply to transducer 21 and its corresponding valve 61.

In response to a command to reduce the tracking pressure, the electronic feedback circuit will partially close the orifice of the voltage sensitive orifice valve. This action is not always sufficient to pull the pressure down. The programmable tracking regulator needs a relief mechanism in order to vent excess gas. In one embodiment, the tracking pressure regulator has a small leak to atmosphere, throttled by means of a capillary tubing connection to minimize the rate of the gas leak. In this way, the pressure will plunge as soon as the source orifice is reduced. In a second embodiment, the small leak is connected to a vacuum reservoir, and the pressure can plunge below atmospheric pressure if this is required for proper operation of the microfluidic circuit. In a third embodiment shown in FIG. 7, active control of venting is effected by an additional voltage sensitive orifice valve 65 operating inversely proportional to the pressurizing valve 60 illustrated in FIG. 7. The operational amplifiers 485, 490 and the power transistor 500 provide the control current for the valve 65.

Figure 8:
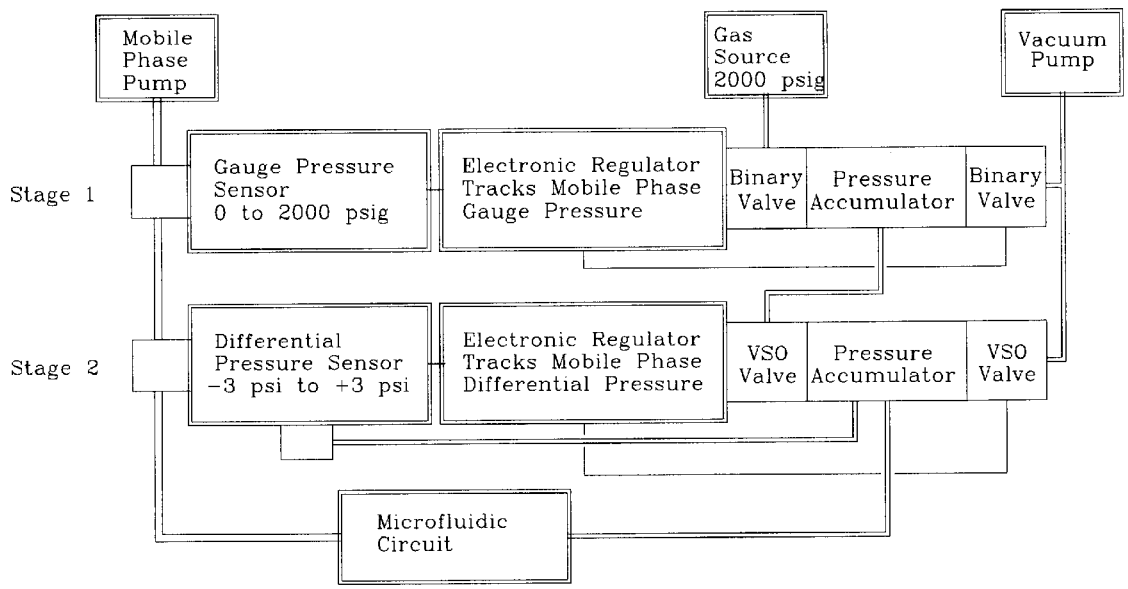
FIG. 8 is a block diagram showing an extension of the single-stage tracking pressure regulator to a two-stage tracking pressure regulator.

FIG. 8 is a block diagram of an extension of the single-stage tracking pressure regulator described heretofore. The single-stage device has a pressure range limited to a maximum of about 150 psi. because the voltage sensitive orifice valve currently available has a maximum pressure rating of this value. In order to reach much higher pressures, another stage can be added, whereby the maximum pressure drop across the valve does not exceed 150 psi. The gauge pressure required within the accumulator cavity may be as high as 2000 psi. This can be accomplished by adding to the device a first stage that tracks the gauge pressure of the mobile phase, and adding an increment of up to 150 psi to this pressure. This regulated tracking pressure can be used as the input to the differential tracking regulator cited previously. The pressure need not be extremely precise because it is given a very wide margin. However, the first stage should respond more slowly to changes in the mobile phase pressure than the differential second stage described heretofore. The damped response is desirable in order to avoid instability and oscillations. The extension allows for a much wider range of operation without a sacrifice in resolution. This two-stage version of the regulator is required to reach much higher-pressures.

Figure 9:
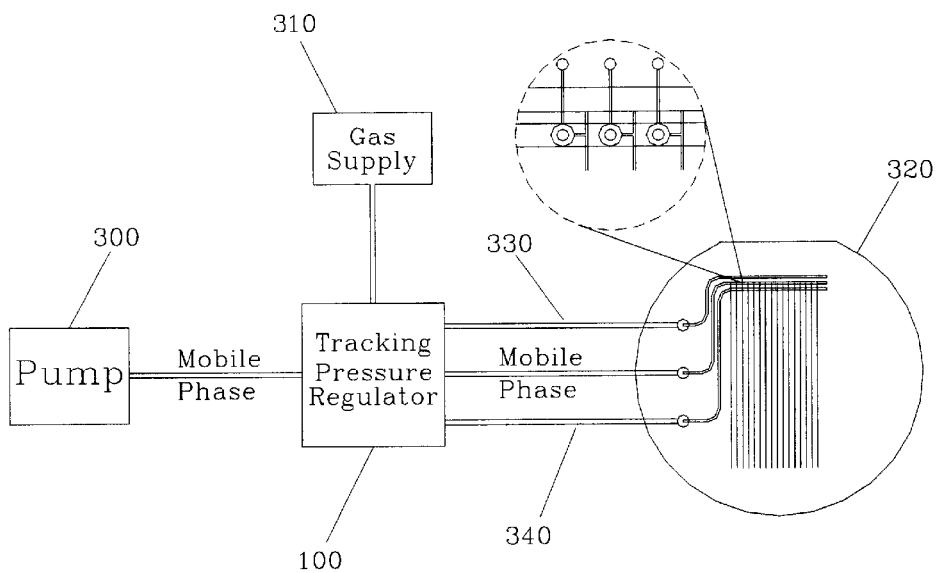
FIG. 9 is a schematic diagram of the tracking pressure regulator used in conjunction with a system that includes an array of capillary chromatography columns on a silica chip.

FIG. 9 illustrates one application of the present invention where the tracking pressure regulator is used in conjunction with a capillary chromatography microfluidic system. In this application, tracking pressure regulator 100 is placed in line between a pump 300 and a chromatography chip 320. The pressures of two control lines (330 and 340), adjusted as previously described by pressure regulator 100 through gas supply 310, are the output of the regulator, and are in communication with ports (see enlarged blowup) on the chromatography chip to allow external control of fluid motion on the chip. Samples at atmospheric pressure are introduced through openings on the surface of the chromatography chip when the mobile phase is stationary. As the mobile phase pressure increases, the control pressures generated by the tracking pressure regulator block flow outward through these openings, thereby preventing mobile phase and samples from spraying out of the entry ports. Donuts formed in a liquid capillary as described in the aforementioned '471 are used to provide external control of fluid motion and sample injection. To enable such operation, the pressure in the control lines 330, 340 needs to be maintained at the common mode (mobile phase) pressure, or slightly above or below the mobile phase pressure. The use of the tracking pressure regulator of the present invention accomplishes this result.

What is claimed is:

1. A tracking pressure regulator, comprising:
   a controller;
   a first pressure transducer in communication with the controller, the pressure transducer being positioned to measure differential pressure between first and second fluid streams, the transducer adapted to send a signal to the controller indicative of that differential pressure, and wherein the second fluid stream is a mobile phase in fluid communication with a high performance liquid chromatographic chip;
   a valve through which the first fluid stream flows, the valve being responsive to the controller, whereby the flow of the first fluid stream out of the valve is regulated based upon the differential pressure.

2. The tracking pressure regulator of claim 1, further comprising a second pressure transducer positioned to measure a second differential pressure between the second fluid stream and a third fluid stream, and a second valve through which the third fluid stream flows, the second valve being responsive to the controller whereby the flow of the third fluid stream out of the second valve is regulated based upon the second differential pressure.

3. The tracking pressure regulator of claim 1, further comprising a cavity adjacent to the first pressure transducer, and a tube passing through the cavity, the tube containing the second fluid stream.

4. The tracking pressure regulator of claim 3, further comprising a substantially incompressible fluid in the cavity surrounding the tube and in intimate contact with the pressure transducer.

5. The tracking pressure regulator of claim 2, further comprising a cavity between the first and second pressure transducers, and a tube in the cavity, the tube containing the second fluid stream.

6. The tracking pressure regulator of claim 5, further comprising a substantially incompressible fluid in the cavity surrounding the tube and in intimate contact with the first and second pressure transducers.

7. The tracking pressure regulator of claim 1, wherein the regulator is controlled remotely.

8. A system for delivering a liquid sample to a point of use which comprises:
   a storage volume in fluid communication with a gas,
   an inlet capillary conduit for receiving a liquid sample in fluid communication with the storage volume,
   an outlet capillary conduit for receiving a liquid sample in fluid communication with the storage volume,
   the storage volume being dimensioned to form a meniscus on a capillary liquid stream passing within the storage volume,
   a capillary gate in fluid communication with the outlet capillary conduit, and in fluid communication with a gas, and being dimensioned to permit liquid to flow through the capillary gate between the outlet capillary conduit and a drain capillary conduit,
   and a tracking pressure regulator for controlling gas pressure in the storage volume, the tracking pressure regulator comprising:
      a controller;
      a pressure transducer in communication with the controller, the pressure transducer being positioned to measure differential pressure between the gas and first and second fluid streams, the transducer adapted to send a signal to the controller indicative of that differential;
      a valve through which the gas flows, the valve being responsive to the controller, whereby the flow of the gas out of the valve and into the storage volume is regulated based upon the differential.

9. The system of claim 8, further comprising a second pressure transducer positioned to measure a second differential pressure between the second fluid stream and a third fluid stream, and a second valve through which the third fluid stream flows, the second valve being responsive to the controller whereby the flow of the third fluid stream out of the second valve is regulated based upon the second differential pressure.

10. The system of claim 8, wherein the second fluid stream is a mobile phase in fluid communication with a high performance liquid chromatographic chip.

11. A method of controlling pressure differences between connected pressure control nodes, comprising:

providing a sealed housing containing a first and second measured fluid stream and a reference fluid stream;

sensing the differential pressure between the first measured fluid stream and the reference fluid stream with a first pressure transducer;

regulating the flow of the first measured fluid stream based upon the differential;

sensing the differential pressure between the second measured fluid stream and the reference fluid stream with a second pressure transducer; and regulating the flow of the second measured fluid stream based upon the differential.

* * * * *